United States Patent [19]
Uesugi et al.

[11] Patent Number: 5,866,192
[45] Date of Patent: Feb. 2, 1999

[54] PROCESS FOR PRODUCING EDIBLE MATERIAL FROM SOYBEANS

[75] Inventors: Shigemi Uesugi; Youichi Fukuda; Yasue Nagao, all of Ibaraki-ken, Japan

[73] Assignee: Fuji Oil Company, Limited, Osaka-fu, Japan

[21] Appl. No.: 938,744

[22] Filed: Sep. 26, 1997

[51] Int. Cl.⁶ .............................. A23L 1/20; A23B 4/03
[52] U.S. Cl. .................... 426/634; 426/652; 426/455; 426/456; 426/465; 426/473; 426/482
[58] Field of Search ................... 426/634, 652, 426/455, 456, 465, 473, 482

[56] References Cited

U.S. PATENT DOCUMENTS

| | | | |
|---|---|---|---|
| 4,041,187 | 8/1977 | Nelson et al. | 426/598 |
| 4,828,869 | 5/1989 | Doi et al. | 426/656 |

FOREIGN PATENT DOCUMENTS

| | | |
|---|---|---|
| 0289060 | 11/1988 | European Pat. Off. . |
| 1453438 | 10/1976 | United Kingdom . |

OTHER PUBLICATIONS

Database WPI, Section Ch, Week 8549, Derwent Publications Ltd., London, GB; AN 85–307709, XP002051644 & JP 60 214 855 A (Narabe T), Oct. 28, 1985, abstract.

Patent Abstracts of Japan, vol. 012, No. 050 (C–476), Feb. 16, 1988, & JP 62 198364 A (Fuji Oil Co Ltd), Sep. 2, 1987, abstract.

Tuley, "Sunrise For Soya", Food Manufacture, vol. 66, No. 6, Jun. 1, 1991, pp. 22–24.

Primary Examiner—Nina Bhat
Attorney, Agent, or Firm—Wenderoth, Lind & Ponack, L.L.P.

[57] ABSTRACT

An edible material containing soybean cell walls having a good taste is produced by providing dehulled and hypocotyl-removed soybeans without substantial swelling by water absorption; soaking and heating the soybeans in hot water to which an alkali has been added under the conditions of: $\mathrm{Log(Hr)} + 0.0333 \; \mathrm{Temp} \geq 2.4$, wherein $\mathrm{Log(Hr)}$ represents the common logarithm (to base ten) value of a soaking time (hours), and Temp represents a soaking temperature (°C.); and then crushing the soybeans.

13 Claims, 2 Drawing Sheets

PROCESS FOR PRODUCING EDIBLE MATERIAL FROM SOYBEANS

BACKGROUND OF THE INVENTION

1. Field of the Invention

The present invention relates to a process for producing an edible material, i.e., a material to be used as an ingredient of foodstuffs, from soybeans. More specifically, it relates to a process for producing an edible material containing soybean cell walls, which has good taste and mouthfeel and which can be used for the same use as that of bean jam, mashed potato, hard-boiled egg yolk and the like or can be used for gelation.

2. Description of the Related Art

A bean jam is an edible material having a granular or particulate appearance with less crumbly property and, usually, it is made from red beans ("adzuki" beans) by conversion of starch particles enveloped in cell membranes of red beans to $\alpha$-starch, and penetration of sugar into the beans to delay retrogradation of the $\alpha$-starch to $\beta$-starch. The mashed potato is food or an ingredient of foodstuffs in which starch is enveloped in cells and which has particulate appearance or cream-like mouthfeel. Also, an egg yolk of hard-boiled egg has such unique mouthfeel that it is crumbled into particles upon pressing it in the mouth, and is different from an egg yolk obtained by opening an egg, breaking the egg yolk membrane and heat-coagulating it, because the latter egg yolk has elastic rubber-like mouthfeel.

In case of soybeans which contain little starch particles, it has also been known that a bean jam-like edible material can be made therefrom. However, any product containing soybean cell walls and having good taste and mouthfeel is not yet obtained.

For example, although a method using defatted soybeans or soybean flour made from defatted soybeans as a raw material has been known, there is a problem that, generally, the product obtained has rough mouthfeel and astringent taste. In order to improve the taste, sometimes, the product is subjected to washing with alcohol or the like. However, this requires a complicated processing step.

In order to solve the problem, to use whole soybeans as a raw material has been proposed. When using whole soybeans, as disclosed in JP-A 61-104758, JP-A 62-138161, etc., generally, they are soaked and swollen in water, followed by processing. However, another problem is a bad taste due to "boiled bean flavor" in addition to insufficient removal of undesired "bean flavor".

The main object of the present invention is to develop an edible material containing soybean cell walls, which has good taste and mouthfeel and which can be used for the same use as that of bean jam, mashed potato, hard-boiled egg yolk and the like or can be used for gelation.

This object as well as other objects and advantages of the present invention will become apparent to those skilled in the art from the following description with reference to the accompanying drawings.

SUMMARY OF THE INVENTION

Figure 1:
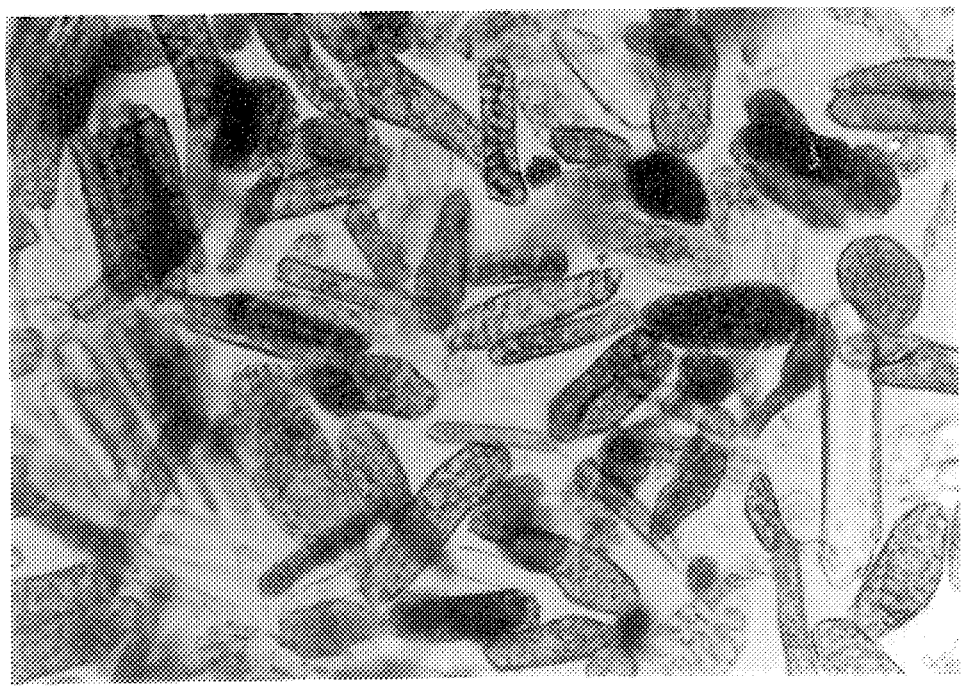
FIG. 1 is a microphotograph (×100) of the edible material from soybeans obtained in Example 1, hereinafter.

According to the present invention, there is provided a process for producing an edible material containing soybean cell walls which comprises the steps of:

providing dehulled and hypocotyl-removed soybeans without substantial swelling by water absorption;

soaking and heating the soybeans in hot water to which an alkali has been added under the conditions of:

$$\text{Log(Hr)} + 0.0333 \text{ Temp} \geq 2.4$$

wherein Log(Hr) represents the common logarithm (to base ten) value of a soaking time (hours), and Temp represents a soaking temperature (°C.); and crushing the soybeans.

DETAILED DESCRIPTION OF THE INVENTION

The present invention will be illustrated in detail hereinafter.

Dehulling and removal of hypocotyls can be carried out by a known method. For example, JP-A 62-198364 discloses a preferred method, wherein whole soybeans are dried with heating at a temperature of 60° C. or higher and then treated with a grinder. Of course, any other method can be employed. In any event, if dehulled and hypocotyl-removed whole soybeans are not used as the raw material, it is difficult to obtain a product of satisfactory quality in respect of both taste and mouthfeel.

In the present invention, desirably, dehulling and removal of hypocotyls are carried out with minimizing breaking and pressing to squeeze the soybeans, i.e., with maintaining cells of soybeans without undergoing breaking as much as possible. Since enzymes such as lipoxygenase, etc. are still alive in cells of soybeans which are merely subjected to dehulling and removal of hypocotyls, though they are in an inactive state, they are apt to be activated by breaking soybean cells to form bad taste or flavor components. Then, dehulled and hypocotyl-removed soybeans are desirably split soybeans such as those split into halves to four pieces which have not undergone breaking.

Defatted soybeans in which cells are broken by pressing to squeeze out the oil or soybean flour are different from the above-described dehulled and hypocotyl-removed soybeans and they are not suitable for the raw material of the present invention to be soaked in hot water.

The soybean raw material which is substantially free from swelling by water absorption is added to hot water, and soaking and heating is carried out under the conditions that the value of Log(Hr)+0.0333 Temp is 2.4 or higher. Hereinafter, this value is referred to as the heating value. The heating value is preferably 2.6 to 3.5, more preferably, 2.7 to 3.0. If this value is too small, the improvement of taste and flavor is insufficient. When the value is 2.4 or larger but smaller than 2.6, cell walls per se apt to be broken in the subsequent crushing step. Perhaps, this is resulted from insufficient decomposition of the intercellular material, pectin ($\beta$-elimination) or insufficient denaturation of protein in soybean cells. In particular, it is difficult to produce an edible material wherein the contents of soybean cells surrounded by cell walls are predominantly observed as particles derived from soybeans. When the heating value is too large, sometimes, undesired boiled-bean flavor or another bad taste may be caused.

The soaking temperature, Temp, is 80° C. or higher, preferably, 85° C. or higher. The heating time varies depending upon the temperature. For example, the heating is carried out for about 10 minutes or longer, preferably about 16 to 130 minutes, more preferably about 20 to 41 minutes in case at 95° C.

The term "without substantial swelling by water absorption" or "substantially free from swelling by water absorption" used herein means soybeans which do not have any substantial swollen appearance. Of course, normally marketed dry soybeans having a moisture content of about 12.5% are included in such a state and, for example, soybeans merely washed with water to remove dust, etc. and having a moisture content of about 20% are also included in such a state. In case of swollen soybeans, a dormant state of soybean seeds is changed toward an activated state and a bad taste is caused due to activation of enzymes in the seeds, etc. However, when soybeans without swelling by water absorption are soaked in hot water, enzymes which cause a bad taste are quickly inactivated and it is possible to minimize formation of a bad taste.

In the present invention, when carrying out the soaking and heating, an alkali, preferably, a bicarbonate such as sodium bicarbonate is added to hot water, normally, in concentration of 0.01 to 4% by weight. This addition of an alkali can inhibit the activity of β-glucosidase which has relatively higher thermal resistance. In addition, since the decomposition (β-elimination reaction) of pectin which is an intercellular material is promoted by making the hot water basic with addition of the alkali, cells are easy to separate into pieces without breaking thereof upon crushing.

The soybeans thus soaked and heated in hot water are subjected to crushing. At this stage, cooling of the soybeans is not required. Rather, if the soybeans soaked and heated at the heating value of 2.4 to smaller than 2.6 are cooled, fluidity of the intercellular material, pectin, is decreased and there is a possibility that it causes breaking of soybean cell walls per se upon crushing. That is, desirably, the crushing is carried out after making the intercellular material fragile by increasing the heating value to 2.6 or higher by soaking and heating, or is carried out after heating at the heating value of 2.4 to smaller than 2.6 and before it is cooled. For obtaining a more bland taste, it is effective to drain water from the soybeans between the soaking in hot water and the crushing to remove soluble materials extracted with the hot water. However, for maintaining improved bean flavor, draining water from the soybeans is not required. To the contrary, if necessary, water can be added according to operation of a particular crushing apparatus.

Desirably, the crushing is carried out at least in such a degree that individually separated cell walls are predominantly observed. When the crushing is insufficient, that is, when cell walls are not separated individually and aggregates of plural cells are still predominantly observed, the edible material obtained has inferior mouthfeel such as rough mouthfeel. The term "predominantly observed" used herein means "remarkably observed".

Thus, the crushing is stopped in such a degree that the contents of soybean cells surrounded by cell walls are predominantly observed, thereby providing excellent granular or particulate mouthfeel to the resulting edible material more effectively. To the contrary, when the contents of soybean cells are observed increasingly outside of cells, the granular or particulate mouthfeel of the resulting edible material is decreased and creamy mouthfeel is increased together with soybean protein properties. Such edible material can be used for gelation.

As means for the crushing, a wide variety of crushing apparatuses such as from a home mixer to stone or ceramic rolls or a homogenizer can be used. For stopping the crushing in such a degree that the contents of soybean cells surrounded by cell walls which are not broken are predominantly observed, such crushing can be simply and readily carried out by treatment with stone or ceramic rolls at little pressure between rolls (to adjust the gap between rolls so as to bring one roll into contact with the other roll is sufficient). When treatment with stone or ceramic rolls is carried out by applying pressure to the gap between rolls, the edible material in which the contents of soybean cells are outside of cell walls can be readily prepared. Even for this crushing to get the contents out of the cell walls, such vigorous crushing conditions as treating with a homogenizer to break many soybean cell walls are not required. Rather, as attention should be paid to avoid formation of certain components for causing a bad taste which are considered to be derived from soybean cell wall tissue, the crushing can be carried out by pulverizing soybeans with a sharp edge rather than homogenizing. In such a case, the resulting edible material has more creamy mouthfeel with less. problems regarding tastes. In addition, the degree of crushing can be adjusted by using UHT treatment accompanied by steam blow and pressure release.

The accompanying FIG. 1 is a microphotograph, wherein the soybean particles are in the state that individually separated cell walls are predominantly observed and that the contents of soybean cells surrounded by cell walls which are not broken are predominantly observed. The particle size after crushing is in the range of from 50 to 500 μm in case of obtaining the edible material having particulate appearance.

The crushed material obtained above is subjected to UHT treatment, dehydration, drying and the like, if necessary, and it can be used as the edible material having excellent taste and mouthfeel. In particular, the edible material whose crushing has been carried out in such a degree that the contents of soybean cells surrounded by cell walls which are not broken are predominantly observed has good particulate mouthfeel and can be used for the same way as that of a bean jam, mashed potato, an egg yolk of hard-boiled egg and the like. On the other hand, the edible material whose crushing has been carried out vigorously so that the contents of soybean cells are outside of cells can be used for gelation, for example, as a binder of hamburger, an ingredient of "gammodoki (fried bean curd mixed with pieces of vegetables and seaweed)" or an ingredient of "tofu (bean curd)"—like food.

In addition to the edible material as such, the edible material can be flavored with various seasoning, spices and the like. For example, when a sweetener such as sugar, maltose or the like is added to the edible material (e.g., by using 100 wt % or more based on solids of the soybean crushed product), the resultant edible material has the same taste as that of a conventional red bean jam and it can be used for various Japanese cakes according to the same manner as that of a conventional red bean jam. When a sweetener is used in an amount smaller than the above, the resultant edible material can be used according to the same manner as conventional mashed potato, i.e., addition to salad or the like to improve a taste and a nutritive value. Further, when the edible material is flavored with a seasoning such as ketchup, mayonnaise, mustard or the like, the resultant edible material can be used for various daily dishes, fillings and the like.

Alternatively, such a unique mouthfeel as an egg yolk of hard-boiled egg can be improved by further subjecting the crushed product to the following step. That is, after the above crushing step, a binder can be added to the resultant crushed product to provide binding properties or, preferably, the moisture content of the crushed product is adjusted to about 30 to 70% so as to provide plasticity. The proportion of the crushed product and a binder is such that the amount of the crushed product (weight of the product without drying) is about 25 to 90 wt %, preferably about 40 to 80 wt % and more preferably about 50 to 80 wt % based on the total weight of the crushed product and the binder. When the crushed product is too little, particulate appearance cannot be provided and the resultant edible material does not have hard-boiled egg yolk like mouthfeel. On the other hand, if the amount of the binder is too much, particles hardly bind to one another and it is difficult to provide the resultant edible material with such a mouthfeel that the material is separated into pieces during eating. Examples of the binder include heat coagulable proteins such as soybean protein and meat proteins of poultry, animal, fish and shellfish, and cold coagulable protein such as gelatin. In case of using a heat coagulable protein, for example, heating is carried out at about 80° to 100° C. for about 5 to 60 minutes. In case of using a cold coagulable protein, for example, coagulation is carried out by cooling in water or a refrigerator after molding.

Preferably, the binder to be used herein is one which does not produce too strong binding power. Then, for example, in case of using soybean protein as the binder, it is preferred to use hydrous soybean protein obtained by adding water thereto in an amount 3 times or more, preferably 4 to 8 times as much as the dried soybean protein.

When the above adjustment of the moisture content is carried out instead of using the binder, for example, the crushed product is dried and then water is added thereto. Alternatively, the dried crushed product is mixed with the crushed product which is not dried.

As described hereinabove, according to the process of the present invention, the edible material having a good taste with little undesired bad bean taste can be obtained. In addition, various confections and food can be produced by using the edible material produced by the process of the present invention.

The following examples and comparative examples further illustrate the present invention in detail. However, they are not to be construed to limit the scope of the present invention. All the "percents" used in the examples are by weight.

EXAMPLE 1

According to the method disclosed in JP-A 62-198364, U.S. whole soybeans were dried by heating at 60° C. or higher, followed by grinding to obtain dehulled and hypocotyl-removed soybeans. The soybeans were split into halves, put into 3.5-fold volume of boiling water containing 0.3% sodium bicarbonate and heated at 95° C. for 30 minutes (heating value: 2.86). Then, water was drained from the soybeans and crushed with stone rolls without cooling to obtain the desired soybean edible material (moisture content: 60%). When the resultant edible material was observed with a microscope, as shown in FIG. 1, particulate soybean cells which were surrounded cell walls separated into pieces without breaking (the contents of soybean cells were surrounded by cell walls which were separated into pieces but were not broken) were predominantly observed. An undesired bean flavor was scarcely recognized.

EXAMPLE 2

According to the same manner as described in Example 1, soybeans were soaked in hot water and water was drained from the soybeans. Then, the swollen soybeans together with twice volume of the boiled water were crushed with a home mixer and then dehydrated to obtain the desired soybean edible material. When the resultant material was observed with a microscope, particulate soybean cells surrounded by cell walls separated into pieces without breaking were predominantly observed. The material had a good taste.

EXAMPLE 3

According to the same manner as described in Example 1, soybeans were soaked in hot water. Then, the soybeans were crushed with a home mixer without draining and cooling and dehydrated to obtain the desired soybean edible material. When the resultant material was observed with a microscope, particulate soybean cells surrounded by cell walls separated into pieces without breaking were predominantly observed. The material had a good taste.

EXAMPLE 4

According to the same manner as described in Example 1, the desired soybean edible material was obtained except that the heating was carried out at 85° C. for 60 minutes (heating value: 2.83). When the resultant material was observed with a microscope, particulate soybean cells surrounded by cell walls separated into pieces without breaking were predominantly observed. The material had a good taste.

EXAMPLE 5

According to the same manner as described in Example 1, the desired soybean edible material was obtained except that the heating was carried out at 120° C. for 5 minutes (heating value: 2.92). When the resultant material was observed with a microscope, particulate soybean cells surrounded by cell walls separated into pieces without breaking were predominantly observed. The material had a good taste.

COMPARATIVE EXAMPLE 1

U.S. whole soybeans were split into halved without dehulling and removal of hypocotyls. Then, according to the same manner as described in Example 1, the soybeans were soaked in hot water, followed by draining water and crushing. However, the resultant product had bad bean tastes such as astringency and the like. In addition, the product had undesired rough mouthfeel.

COMPARATIVE EXAMPLE 2

Figure 2:
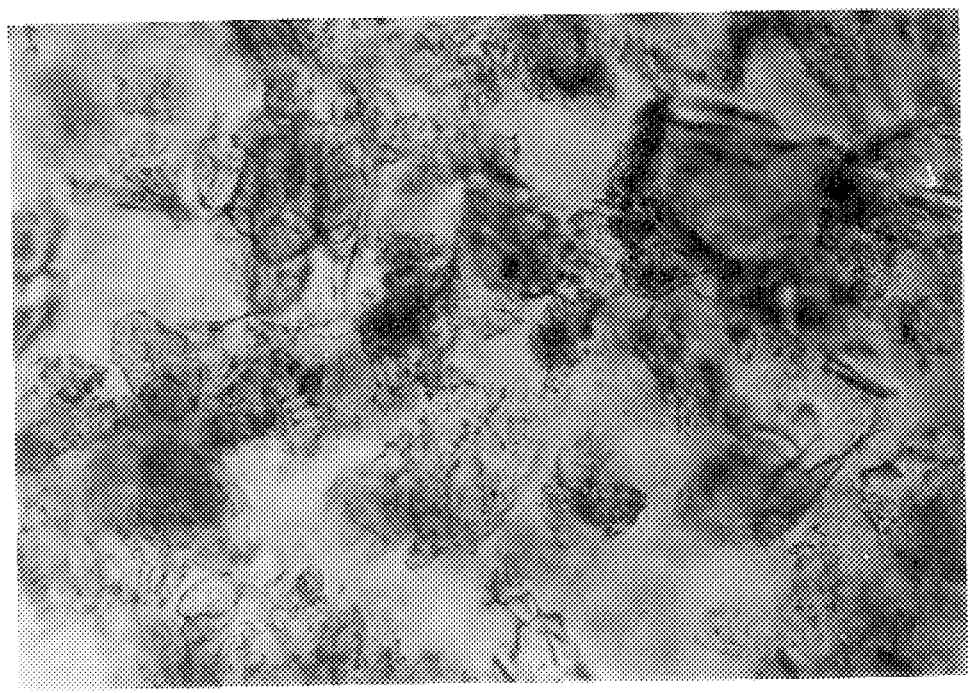
FIG. 2 is a microphotograph (×100) of the ground product of soybeans obtained in Comparative Example 2, hereinafter.

U.S. whole soybeans were treated according to the method disclosed in JP-A 62-198364 to obtain half-split soybeans. They were pressed to squeeze out the oil and defatted with hexane. The defatted soybeans thus obtained were put into 3.5-fold volume of boiling water containing 0.3% sodium bicarbonate and heated at 95° C. for 30 minutes. Then, soybeans were crushed with stone rolls without cooling. However, the resultant product had bad taste and mouthfeel. When the resultant product was observed with a microscope, as shown in FIG. 2, original shapes of cells were almost disappeared and were quite different from the desired edible material as shown in FIG. 1.

COMPARATIVE EXAMPLE 3

According to the same manner as described in Example 1, a soybean edible material was obtained except that the heating was carried out at 80° C. for 30 minutes (heating value: 2.36). However, the resultant product had inferior mouthfeel and taste in comparison with the edible product of Example 1.

EXAMPLE 6

Refined sugar (60%), starch syrup (11%), salt (0.5%) and an appropriate amount of water were added to the edible material (100%) of Example 1 in the form of a crushed material and kneaded over a high flame. When a suitable moisture content was obtained by kneading, the fire was put out to obtain soybean jam similar to no-sweetened bean jam made from adzuki. The resultant product had good taste and mouthfeel.

EXAMPLE 7

Tomato ketchup (7%) and salt (1%) were added to the soybean edible material obtained in Example 1 and the mixture was thoroughly mixed to obtain a filling having tomato ketchup taste.

EXAMPLE 8

Minced beef (5%) which had been heated, finely chopped onion (5%), salt (1%), synthetic seasoning (0.5%) and appropriate amounts of pepper and nutmeg were added to the soybean edible material obtained in Example 1. The mixture was uniformly mixed, crumbed and fried to obtain nourishing croquette-like food containing soybeans.

EXAMPLE 9

The soybean edible material obtained in Example 1 was added to a salad instead of mashed potato in an amount of 20% to obtain a nourishing salad containing soybeans.

EXAMPLE 10

Agar powder (2 g), granulated sugar (50 g) and salt (1 g) were added to water (400 ml) and the mixture was boiled. Then, the soybean jam obtain in Example 6 (300 g) was added thereto. The mixture was boiled down to 650 g and placed in a mold to obtain soft Japanese bean jelly-like food.

EXAMPLE 11

The crushed soybean edible material obtained in Example 1 (30 g) and water (3 g) was added to fluid egg yolk (20 g) and the mixture was mixed to obtain a paste. This was poured on powder paper placed in 3 petri dishes of 9 cm in diameter, steamed for 30 minutes and cooled to obtain food having mouthfeel of egg yolk of hard-boiled egg.

EXAMPLE 12

A binder was prepared by mixing isolated soybean protein (FUJIPRO-SE manufactured by Fuji Oil Co., Ltd., 40 g), water (200 g), soybean refined oil (40 g) and salt (4.2 g) with a food cutter. To this binder (240 g) were added the crushed soybean edible material obtained in Example 1 (360 g) and egg white (31.2 g) and they were mixed to obtain a paste. The paste was deaerated and each 200 g portion thereof was stuffed and sealed in a synthetic casing tube of 35 mm of folding diameter. They were heated in a hot bath at 80° C. for 30 minutes and cooled to obtain stuffed egg yolk-like food.

EXAMPLE 13

According to the same manner as described in Example 1, the desired soybean edible material was obtained except that the crushing was carried out with ceramic rolls (pressure between rolls: 5 kg/cm$^2$). When the resultant material was observed with a microscope, the contents of soybean cells were outside of cell walls which were separated into pieces observed. An undesired bean flavor was scarcely recognized.

EXAMPLE 14

Minced beef (400 g), one finely chopped onion and on egg were added to the soybean edible material obtained in Example 13. The taste was controlled with salt. The mixture was mixed, molded and fried to obtain hamburger having good taste.

What is claimed is:

1. A process for producing an edible material comprising soybean cells having cell walls and having improved granular or particulate mouthfeel, which comprises the steps of:

providing dehulled and hypocotyl-removed soybeans without substantial swelling by water absorption;

soaking and heating the soybeans in hot water to which an alkali has been added under the conditions of:
$Log(Hr)+0.0333\ Temp \geq 2.4$
wherein Log(Hr) represents the common logarithm (to base ten) value of a soaking time (hours), and Temp represents a soaking temperature (°C.); and crushing the soybeans to predominantly separate the soybeans into individual soybean cells having cell walls without breaking the cell walls.

2. A process according to claim 1, wherein the soaking and heating are carried out under the conditions of
$2.6 \leq Log(Hr)+0.0333\ Temp \leq 3.5$.

3. A process according to claim 1, wherein the soaking and heating are carried out under the conditions of Temp $\geq 85°$ C.

4. A process according to claim 1, wherein the alkali added is a bicarbonate.

5. A process according to claim 1, wherein the crushed product is further processed together with saccharides and/or seasoning to obtain a paste.

6. A process according to claim 1, wherein the crushed product is further bound with a binder.

7. A process according to claim 1, wherein the moisture content of the crushed product is adjusted to 30 to 70%.

8. A process according to claim 6, wherein the proportion of the crushed product and the binder is such that the amount of the crushed product is 25 to 90% by weight based on the total weight of both the crushed product and the binder.

9. A process according to claim 6, wherein the binder contains heat coagulable protein or cold coagulable protein.

10. A soybean edible material comprising separate individual soybean cells having unbroken cell walls.

11. A soybean edible material according to claim 10, wherein the main components present in the individual soybean cells are soybean protein and soybean oil.

12. A soybean edible material according to claim 10, wherein the soybean cells with cell walls have a size in the range of 50 to 500 μm.

13. A soybean edible material according to claim 11, wherein the soybean cells with cell walls have a size in the range of 50 to 500 μm.

* * * * *

UNITED STATES PATENT AND TRADEMARK OFFICE
CERTIFICATE OF CORRECTION

PATENT NO. : 5,866,192
DATED : February 2, 1999
INVENTOR(S) : Shigemi UESUGI et al.

It is certified that error appears in the above-indentified patent and that said Letters Patent is hereby corrected as shown below:

On the title page, insert the following:

--Foreign Application Priority Data

Sep. 30, 1996 [JP]   Japan ............... 8-258732--

Signed and Sealed this

Twentieth Day of July, 1999

Attest:

Q. TODD DICKINSON

*Attesting Officer*            *Acting Commissioner of Patents and Trademarks*